US009920919B2

(12) United States Patent
Matsuoka et al.

(10) Patent No.: US 9,920,919 B2
(45) Date of Patent: Mar. 20, 2018

(54) LIGHT EMITTING DEVICE AND LIGHTING DEVICE PROVIDED WITH SAME

(71) Applicant: Panasonic Intellectual Property Management Co., Ltd., Osaka (JP)

(72) Inventors: Kouichirou Matsuoka, Kyoto (JP); Kazuhiko Hayashi, Osaka (JP); Shintaro Hayashi, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 107 days.

(21) Appl. No.: 15/112,184

(22) PCT Filed: Feb. 17, 2015

(86) PCT No.: PCT/JP2015/000710
§ 371 (c)(1),
(2) Date: Jul. 17, 2016

(87) PCT Pub. No.: WO2015/125457
PCT Pub. Date: Aug. 27, 2015

(65) Prior Publication Data
US 2016/0356485 A1 Dec. 8, 2016

(30) Foreign Application Priority Data

Feb. 20, 2014 (JP) ................................. 2014-030317

(51) Int. Cl.
*F21V 17/00* (2006.01)
*F21V 31/00* (2006.01)
(Continued)

(52) U.S. Cl.
CPC .............. *F21V 31/005* (2013.01); *A61L 2/10* (2013.01); *F21V 3/00* (2013.01); *F21V 7/00* (2013.01);
(Continued)

(58) Field of Classification Search
CPC ........................................... F21V 17/00–17/20
See application file for complete search history.

(56) References Cited

U.S. PATENT DOCUMENTS

2011/0254450 A1* 10/2011 Bergholz ............ F21V 19/0015
315/121
2012/0032197 A1 2/2012 Kurimoto
(Continued)

FOREIGN PATENT DOCUMENTS

JP 1-127246 U 8/1989
JP 6-291369 10/1994
(Continued)

OTHER PUBLICATIONS

International Search Report of PCT application No. PCT/JP2015/000710 dated Apr. 7, 2015.

*Primary Examiner* — Christle I Marshall
(74) *Attorney, Agent, or Firm* — McDermott Will & Emery LLP

(57) ABSTRACT

A light emitting device includes a substrate with a circuit incorporated in the substrate, an interposer having a circuit connected to the circuit of the substrate, a light emitting element disposed on the interposer, a transmissive component disposed positioned to the light emitting element, and a frame body having an opening in which the transmissive component is disposed. The light emitting device further includes a ring-shaped body that encompasses the frame body on the substrate, and a sealant making the substrate and the ring-shaped body tightly contact one another. The frame body is disposed so as to encompass the light emitting element on the substrate. This provides the light emitting device with waterproof function.

4 Claims, 2 Drawing Sheets

(51) Int. Cl.

| | | |
|---|---|---|
| | *F21V 3/00* | (2015.01) |
| | *F21V 17/06* | (2006.01) |
| | *F21V 17/10* | (2006.01) |
| | *F21V 7/00* | (2006.01) |
| | *A61L 2/10* | (2006.01) |
| | *H01L 33/48* | (2010.01) |
| | *F21Y 115/10* | (2016.01) |

(52) U.S. Cl.
CPC ............ *F21V 17/06* (2013.01); *F21V 17/101* (2013.01); *A61L 2209/12* (2013.01); *F21Y 2115/10* (2016.08); *H01L 33/486* (2013.01)

(56) References Cited

U.S. PATENT DOCUMENTS

| | | | |
|---|---|---|---|
| 2014/0291710 | A1 | 10/2014 | Kurimoto |
| 2014/0374776 | A1* | 12/2014 | Nakasuji ............... H01L 25/167 |
| | | | 257/82 |
| 2015/0372204 | A1* | 12/2015 | Matsuoka ............... H01L 33/58 |
| | | | 250/504 R |

FOREIGN PATENT DOCUMENTS

| | | |
|---|---|---|
| JP | 2009-272576 | 11/2009 |
| JP | 2012-054533 | 3/2012 |
| JP | 2013-128064 | 6/2013 |
| JP | 2013-251145 | 12/2013 |

\* cited by examiner

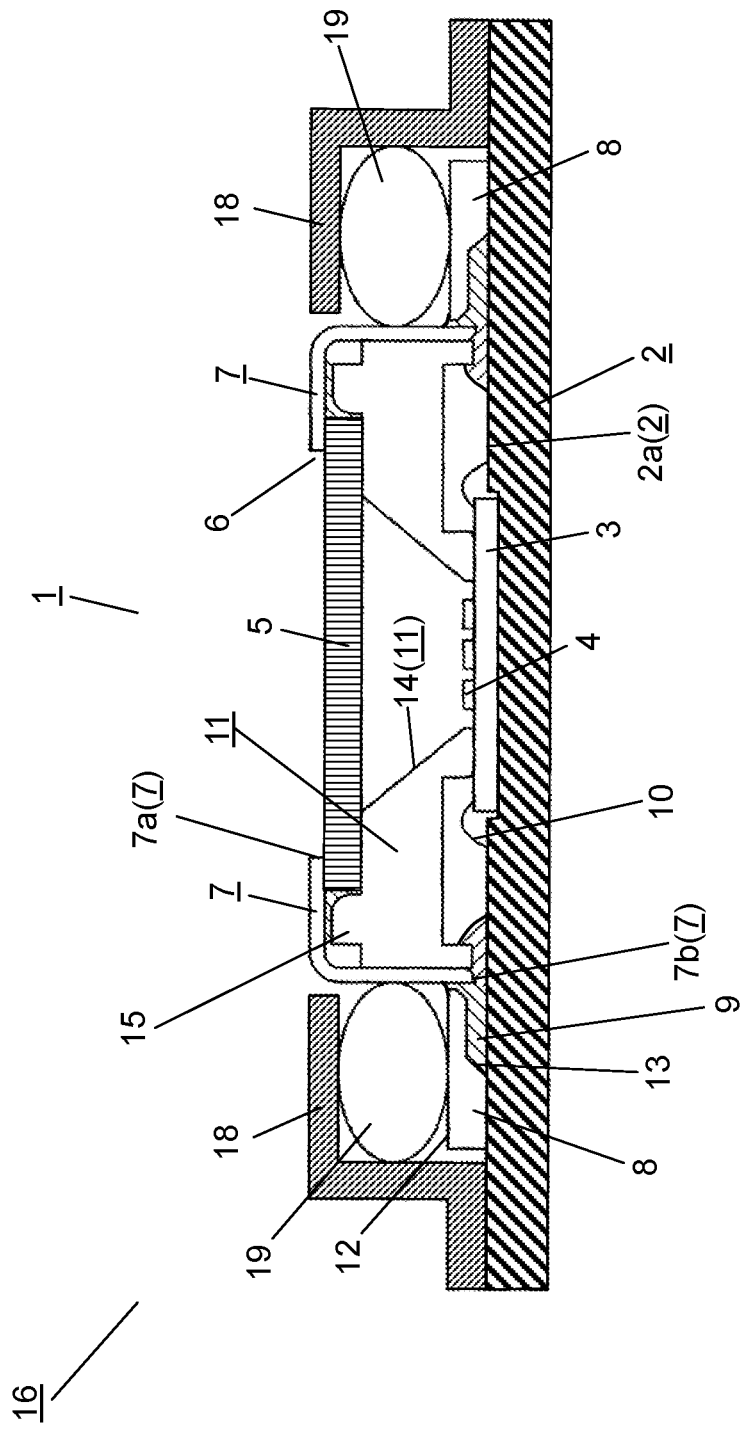

LIGHT EMITTING DEVICE AND LIGHTING DEVICE PROVIDED WITH SAME

THIS APPLICATION IS A U.S. NATIONAL PHASE APPLICATION OF PCT INTERNATIONAL APPLICATION PCT/JP2015/000710.

TECHNICAL FIELD

The present disclosure relates to a light emitting device with waterproof function and a lighting device provided with the light emitting device.

BACKGROUND ART

There has been known a lighting device provided with a light emitting device including a light emitting element such as an LED.

This type of light emitting device is composed of a substrate with a circuit incorporated on its surface, an interposer having another circuit connected to the circuit of the substrate, a package having a recess, and other parts. The interposer is disposed on the substrate, and the light emitting element is disposed on the interposer. Then, the light emitting element is placed inside the recess of the package. Resultingly, the light emitting element is encompassed by the recess of the package on the interposer.

The package further includes a projection projecting outward from the outer circumference along the outer edge of the interposer. The area encompassed by the recess of the package is filled with a light-transmissive filler. The light emitting device is provided with a waterproof resin so as to cover the projection of the package and the outer circumference of the interposer (refer to PTL 1 for example). Accordingly, the light emitting device is used as a sterilizer in a water-related environment such as a hand-wash station.

To sum up, in the light emitting device of PTL 1, the projection of the package and the outer circumference of the interposer are covered with a waterproof resin. This prevents water from reaching the light emitting element through between the package and the interposer.

In the above-described light emitting device, however, the substrate is larger than the interposer and extends beyond the outer edge of the interposer. Then, the waterproof resin covers the projection of the package and the outer circumference of the interposer. This causes the circuit formed on the surface of the substrate that is present around the waterproof resin to be exposed. If water adheres onto the circuit of the exposed substrate in this situation, an electrical trouble can occur.

CITATION LIST

Patent Literature

PTL 1 Japanese Patent Unexamined Publication No. 2012-54533

SUMMARY OF THE INVENTION

The present disclosure provides a light emitting device that prevents water from adhering onto the circuit of the substrate, and a lighting device including the light emitting device.

To sum up, a light emitting device of the present disclosure includes a substrate with a circuit incorporated in the substrate, an interposer disposed on the circuit side of the substrate and having a circuit part connected to the circuit of the substrate, a light emitting element disposed on the interposer, and a transmissive component disposed in accordance with the light emitting element. The light emitting device further includes a frame body having an opening in which the transmissive component is disposed, a ring-shaped body disposed so as to encompass the frame body on the substrate, and a sealant for making the frame body, substrate, and ring-shaped body in tight contact with one another. The frame body is disposed so as to encompass the light emitting element on the substrate.

With this configuration, the interposer, light emitting element, transmissive component, and frame body are disposed on the substrate. The ring-shaped body is disposed on the substrate so as to encompass the frame body. Then, the sealant is disposed that makes the frame body, substrate, and ring-shaped body in tight contact with one another. Resultingly, the substrate is covered with the ring-shaped body, sealant, and interposer in an airtight state. This prevents water entering from the outside from adhering onto the circuit of the substrate.

The lighting device of the present disclosure includes the above-described light emitting device, a case disposed on the substrate and having a ring-shaped part disposed so as to encompass the frame body and ring-shaped body, and a sealing material disposed between the ring-shaped part and the ring-shaped body. Resultingly, a lighting device is achieved that prevents water entering from the outside from adhering onto the circuit of the substrate and has high reliability.

BRIEF DESCRIPTION OF DRAWINGS

FIG. 2 is an outline sectional view of a light emitting device and a lighting device including the light emitting device according to a modified example of the embodiment.

DESCRIPTION OF EMBODIMENT

Figure 1:
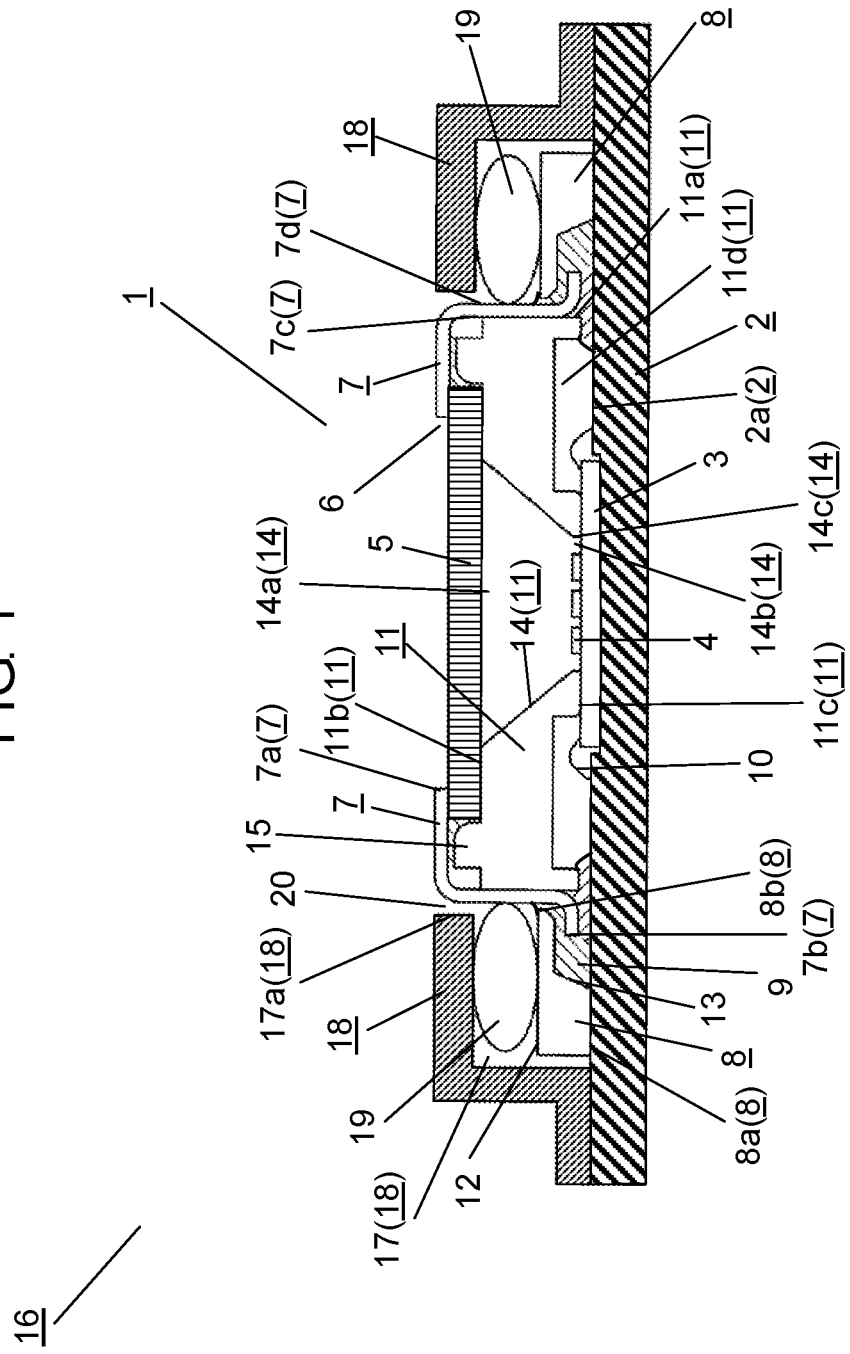
FIG. 1 is an outline sectional view of a light emitting device and a lighting device including the light emitting device according to an embodiment of the present disclosure.

Hereinafter, a description is made of an embodiment of the present disclosure with reference to the related drawings. This embodiment is not intended to limit the scope of the disclosure.

Exemplary Embodiment

Hereinafter, a description is made of a light emitting device and a lighting device including the light emitting device according to an embodiment of the present disclosure, referring to FIG. 1.

FIG. 1 is an outline sectional view of a light emitting device and a lighting device including the light emitting device according to an embodiment of the present disclosure. FIG. 1 shows a state where the light emitting device is incorporated in the lighting device.

First, a concrete description is made of light emitting device 1 of this embodiment.

As shown in FIG. 1, light emitting device 1 of this embodiment is composed of some components such as substrate 2 with a circuit incorporated in the substrate, interposer 3, transmissive component 5, frame body 7, ring-shaped body 8, and positioning component 11. Interposer 3 is disposed on the circuit side of substrate 2 and has a circuit part connected to the circuit of substrate 2. On interposer 3, one or more light emitting elements 4 such as LEDs (Light Emitting Diodes) are disposed. FIG. 1 illustrates an example where three pieces of light emitting elements 4 are disposed. Transmissive component 5 is provided on frame body 7 positioned facing light emitting element 4 on interposer 3. Frame body 7 has opening 6 in which transmissive component 5 is disposed and is formed in a ring shape so as to encompass light emitting element 4 on substrate 2. Ring-shaped body 8 is disposed so as to encompass frame body 7 on substrate 2. Sealant 9 is provided so that frame body 7, substrate 2, and ring-shaped body 8 tightly contact one another to prevent water ingress into the inside of frame body 7.

Light emitting device 1 of this embodiment further includes wire 10 that electrically connects the circuit of substrate 2 with the circuit part of interposer 3. Then, positioning component 11 is provided in contact with interposer 3 in an area except where light emitting element 4 and wire 10 are disposed, to determine the position of transmissive component 5 disposed in opening 6 of frame body 7 facing light emitting element 4.

Light emitting device 1 of this embodiment is configured as described above.

Hereinafter, a more detailed description is made of light emitting device 1 with the above configuration.

Substrate 2 of light emitting device 1 has a circuit incorporated on the surface where interposer 3 is disposed. The circuit of substrate 2 is configured to be able to supply power to light emitting element 4 through wire 10 and interposer 3. Note that substrate 2 of this embodiment has a recess in the surface where interposer 3 is disposed, in a shape conforming to at least the shape of interposer 3. This facilitates positioning interposer 3 to substrate 2; however, it is obvious that a recess does not especially need to be provided in substrate 2.

Interposer 3 is provided in order to supply power to light emitting element 4. Power is supplied to light emitting element 4 through the circuit part of interposer 3 to make light emitting element 4 emit light.

As described above, light emitting element 4, an LED for example, uses power supplied from the circuit part of interposer 3 to emit light with a given wavelength toward the outside. In this embodiment, light emitting element 4 is an LED that emits deep ultraviolet light with a wavelength of 200 nm to 360 nm for example. Resultingly, light emitting element 4 works as a light source with bactericidal effect.

Transmissive component 5 is formed of a plate-like, transparent resin (e.g., acrylic) or glass (e.g., quartz glass), and transmits light emitted from light emitting element 4 toward the outside. Transmissive component 5 is not limited to a plate-like shape, but may be a lens shape having a convex or concave surface or a Fresnel lens shape. In this case, transmissive component 5 is disposed in opening 6 of frame body 7 positioned to light emitting element 4 so that the center of transmissive component 5 is present perpendicularly above the position of substrate 2 where light emitting element 4 is disposed. Concretely, transmissive component 5 is disposed through positioning component 11 as described above.

Frame body 7 is formed of a metallic material such as stainless-steel, aluminum, or Kovar and in a ring shape in a planar view. Inner circumferential surface 7c of frame body 7 is formed in a shape at least so as to be in contact with or to contain outer circumferential surface 11a of positioning component 11. Resultingly, when transmissive component 5 is disposed in opening 6 of frame body 7, outer circumferential surface 11a of positioning component 11 is in contact with inner circumferential surface 7c of frame body 7.

Opening 6 of frame body 7 is formed by bending radially inward the end (hereinafter, described as first end 7a of frame body 7) of frame body 7 where transmissive component 5 is positioned. In this case, opening 6 is formed so that first end 7a is long enough to overlap with at least the outer circumference of transmissive component 5, from inner circumferential surface 7c of frame body 7 corresponding to outer circumferential surface 11a of positioning component 11. Then, first end 7a of frame body 7 extends beyond positioning component 11 and is in contact with the overlapping surface of transmissive component 5. Meanwhile, the end (hereinafter, described as second end 7b of frame body 7) closer to substrate 2 of frame body 7 is formed by being bent toward the outside diameter of frame body 7.

Resultingly, the joint part of transmissive component 5 and positioning component 11 can be protected against water ingress for example at the side of first end 7a of frame body 7. Simultaneously, frame body 7 bent radially outward has an increased area where it is in contact with sealant 9 at the side of second end 7b. Consequently, frame body 7 can be positioned and fixed onto the surface of substrate 2 more tightly.

Ring-shaped body 8 has inner circumference 8b larger than outer circumferential surface 7d of frame body 7 and at the same time smaller than second end 7b, and bottom surface 8a of ring-shaped body 8 disposed at the side of substrate 2 is configured to be a horizontal plane. Further, ring-shaped body 8 is configured so that its surface (top surface) opposite to bottom surface 8a disposed at the side of substrate 2 is configured to be horizontal plane 12. Ring-shaped body 8 has recess 13 that is recessed radially outward from the inside (the side of frame body 7) of bottom surface 8a in contact with substrate 2 to a position (corresponding to inner circumference 8b) beyond second end 7b of frame body 7. Concretely, recess 13 of ring-shaped body 8 is formed recessed radially outward from inner circumference 8b that is positioned higher than the height of frame body 7 from substrate 2. Then, recess 13 is filled with sealant 9 described above. This stops sealant 9 from moving to (entering) between bottom surface 8a directly facing substrate 2 of ring-shaped body 8 and substrate 2. This prevents the degradation of a horizontal state of horizontal plane 12 of ring-shaped body 8 due to ingress of sealant 9.

Second end 7b of frame body 7 is disposed in the space formed by recess 13 of ring-shaped body 8 between recess 13 and substrate 2. This provides a larger area size where sealant 9 is in tight contact with the side of bent second end 7b of frame body 7 than a case where second end 7b of frame body 7 is not bent radially outward for example.

Sealant 9, made of an adhesive such as silicone, fastens parts between positioning component 11, frame body 7, and ring-shaped body 8 in a tight contact manner. Concretely, sealant 9 fastens parts between positioning component 11, second end 7b of frame body 7, and recess 13 of ring-shaped body 8 in a tight contact manner as shown in FIG. 1. Resultingly, sealant 9 fastens ring-shaped body 8 onto the surface of substrate 2. Further, sealant 9 fastens positioning component 11 and frame body 7 onto the surface of substrate 2. Consequently, sealant 9 prevents water from entering light emitting element 4 through around positioning component 11.

Wire 10, made of a bonding wire for example, electrically connects the circuit incorporated on surface 2a of substrate 2 with the circuit part formed of the lead frame of interposer 3. Then, as described above, power supplied to the circuit of substrate 2 is supplied to components such as light emitting element 4 disposed on interposer 3, which causes light emitting element 4 to emit light.

Positioning component 11, formed in a ring shape for example in a planar view, has slope 14 inclined toward one opening (toward transmissive component 5) as the inner circumferential surface as shown in FIG. 1. Positioning component 11 is further provided with projection 15 projecting in the axial direction (the direction in which light is emitted) along the circumferential direction, on end face 11b at the side of opening 14a diameter-expanded by slope 14. Projection 15 is formed so as to project in a shape that has an inner circumferential diameter larger than at least the outer circumferential diameter of transmissive component 5 and at the same time lower than the thickness of transmissive component 5. Resultingly, projection 15 supports transmissive component 5 so as to block diameter-expanded opening 14a of positioning component 11.

Positioning component 11 is further provided with recess 11d the central part of which is recessed along the circumferential direction in end face 11c at the side of opening 14b diameter-reduced by slope 14. Positioning component 11 is rested on interposer 3 in contact with interposer 3 through end face 11c at the side of opening 14b diameter-reduced by slope 14. Further, positioning component 11 is disposed so as to encompass light emitting element 4 disposed on interposer 3 with inner circumferential wall 14c composing diameter-reduced opening 14b. In other words, configuration is made so that positioning component 11 allows light emitting element 4 on interposer 3 to be positioned to the center position of transmissive component 5 disposed vertically above substrate 2.

Positioning component 11 has a given thickness in the axial direction. This allows the height to be positioned at which transmissive component 5 is disposed with respect to light emitting element 4. In this embodiment, above-described positioning component 11 composes a reflector for example that encompasses light emitting element 4 with inner circumferential wall 14c forming diameter-reduced opening 14b. Resultingly, light emitted from light emitting element 4 is collected toward transmissive component 5 by slope 14 of positioning component 11 (i.e., a reflector). Consequently, light from light emitting element 4 can be radiated to the outside with a high emission efficiency.

Light emitting device 1 of this embodiment is configured as described above.

Next, a description is made of lighting device 16 in which light emitting device 1 according to this embodiment is incorporated referring to FIG. 1. Note that lighting device 16 is used as a light source of a sterilizer placed in a hand-wash station for example.

As shown in FIG. 1, lighting device 16 of this embodiment is composed of light emitting device 1 described above, case 18, sealing material 19, and other components. Case 18 has ring-shaped parts 17 that encompass frame body 7 of light emitting device 1. Ring-shaped parts 17 are disposed spaced at given intervals so as to contain ring-shaped body 8 of light emitting device 1. Sealing material 19 is disposed inside ring-shaped part 17 of case 18 on horizontal plane 12 of ring-shaped body 8 of light emitting device 1. Case 18 can be formed of various types of materials such as stainless-steel. If case 18 is formed of a metallic material for example, it is preferable that a circuit is not provided at a position where the case is in contact with the position or an insulating material for example is interposed.

Case 18 has opening 17a formed in ring-shaped part 17. Then, case 18 is disposed so as to expose transmissive component 5 and frame body 7 from opening 17a and so as to cover the surrounding area with ring-shaped part 17. Resultingly, case 18 prevents water ingress into the inside from parts other than opening 17a formed in ring-shaped part 17.

More specifically, case 18 in this embodiment is disposed so as to be able to be in contact with surface 2a of substrate 2 around ring-shaped body 8 of light emitting device 1. This contact causes sealing material 19 disposed between the inner surface of ring-shaped part 17 of case 18 and horizontal plane 12 of ring-shaped body 8 to be pressed. This causes sealing material 19 to be elastically deformed for example to seal the inside.

After all, sealing material 19, made of an O-ring for example, is disposed on horizontal plane 12 of ring-shaped body 8 so as to encompass the surrounding area of frame body 7. When case 18 and light emitting device 1 are combined together, sealing material 19 is pressed by horizontal plane 12 of ring-shaped body 8 and the inner surface of ring-shaped part 17 of case 18, and is deformed. In this case, the part between the inner surface of ring-shaped part 17 and horizontal plane 12 of ring-shaped body 8 is sealed by sealing material 19. Resultingly, sealing material 19 prevents water that has entered through gap 20 between frame body 7 and ring-shaped part 17 for example from passing. This prevents the water from adhering to the circuit formed on surface 2a of substrate 2 outside the outer circumference of ring-shaped body 8. Consequently, lighting device 16 with high reliability can be provided.

Lighting device 16 of this embodiment is configured as described above.

Next, a description is made of effects and advantages of light emitting device 1 and lighting device 16 configured as described above.

First, when light emitting device 1 is combined with case 18 through an adhesive for example, sealing material 19 is pressed by ring-shaped body 8 and the inner surface of ring-shaped part 17. Herewith, above-described lighting device 16 is produced. Then, transmissive component 5 and frame body 7 are exposed from opening 17a formed in ring-shaped part 17 of case 18. At this moment, a space is formed by gap 20 between frame body 7 and ring-shaped part 17.

As a result that ring-shaped body 8 presses sealing material 19, ring-shaped body 8 undergoes an elastic force (a reactive force) from sealing material 19. In this embodiment, however, ring-shaped body 8 and frame body 7 do not directly contact each other, but they contact through sealant 9, and thus an elastic force exerted on ring-shaped body 8 is not transmitted to frame body 7. Accordingly, frame body 7 does not become distorted and deformed. Consequently, the elastic force is not transmitted from first end 7a of frame body 7 to transmissive component 5, which prevents transmissive component 5 from being distorted. Further, a stress on interposer 3 due to positioning component 11 in contact for example can be moderated.

If lighting device 16 is watered from above transmissive component 5 for example, water may enter through gap 20 between ring-shaped part 17 and frame body 7. In this case, the water falls toward surface 2a of substrate 2 along outer circumferential surface 7d of frame body 7 standing upright with respect to surface 2a of substrate 2. Then, the water tends to turn around toward the outer circumference of ring-shaped body 8 from the part between the inner surface of ring-shaped part 17 and ring-shaped body 8. In this embodiment, however, sealing material 19 is pressed by ring-shaped body 8 and the inner surface of ring-shaped part 17 to seal the part between them. Resultingly, sealing material 19 prevents water from entering through the part between the inner surface of ring-shaped part 17 and horizontal plane 12 of ring-shaped body 8. This prevents water from adhering to the circuit of the surface of substrate 2, exposed at the outer circumference of ring-shaped body 8.

Meanwhile, water falling along outer circumferential surface 7d of frame body 7 reaches the part between ring-shaped body 8 and frame body 7. In this embodiment, however, sealant 9 provided between ring-shaped body 8, frame body 7, and positioning component 11 fastens one another in a tight contact manner to block the part between ring-shaped body 8 and frame body 7. This stops the water falling along outer circumferential surface 7d of frame body 7 at the interface of sealant 9 between ring-shaped body 8 and frame body 7. This prevents water from adhering to surface 2a of substrate 2 sealed by sealant 9 itself.

Note that light emitting device 1 according to the present disclosure is not limited to the above-described embodiments, but various types of modifications may be added within a scope that does not deviate from the gist of the present disclosure.

That is to say, in the above-described embodiment, the description is made of the example where second end 7b of frame body 7 is bent toward the outer circumference as shown in FIG. 1, but not limited to this case. For example, as shown by the modified example of the light emitting device and the lighting device including the light emitting device of the embodiment shown in FIG. 2, a configuration may be made in which second end 7b of frame body 7 is not bent toward the outer circumference. Even in this case, a configuration can be achieved in which water does not adhere to surface 2a of substrate 2, in the same way as the above embodiment. This simplifies forming frame body 7 to increase the productivity for example. Moreover, second end 7b of frame body 7 does not need to be inserted into recess 13 of ring-shaped body 8, which makes light emitting device 1 and lighting device 16 further thinner in accordance with an application.

In the above-described embodiment, the description is made of the example of light emitting device 1 configured as lighting device 16 by being combined with case 18 and sealing material 19, but not limited to the case. For example, light emitting device 1 may be singly used. In this case, ring-shaped body 8 is preferably configured to completely cover surface 2a of substrate 2 that is present around transmissive component 5. Resultingly, even if surface 2a of substrate 2 is watered from above light emitting device 1, surface 2a is covered with ring-shaped body 8, sealant 9, frame body 7, and transmissive component 5. This prevents water from adhering onto the circuit of substrate 2.

In the above-described embodiment, the description is made of the example of ring-shaped body 8 configured to have recess 13, but not limited to the case. As long as sealant 9 does not enter between ring-shaped body 8 and substrate 2, and horizontal plane 12 of ring-shaped body 8 can be kept along the surface of substrate 2, ring-shaped body 8 does not need to be provided with recess 13 for example. This increases the productivity of ring-shaped body 8.

In the above-described embodiment, the description is made of the example where sealing material 19 of lighting device 16 is formed of an O-ring, but not limited to the case. For example, another material may be used such as a square ring with a square cross section. After all, any shape may be chosen as long as it has a sealing function. Alternatively, sealing material 19 may be configured to tightly contact frame body 7. This can stop water falling along frame body 7 in the same way as described above.

In the above-described embodiment, the description is made of the example where light emitting device 1 is used as a light source emitting deep ultraviolet light of lighting device 16 (i.e., a light source of a sterilizer), but not limited to the case. For example, light emitting device 1 may be used as various types of light emitting devices and lighting devices as a light source emitting light with various wavelengths. This increases the versatility.

In the above-described embodiment, the description is made of the example where positioning component 11 is provided, but not limited to the case. For example, a configuration without a positioning component provided may be used. In this case, transmissive component 5 needs to be fastened to the inside of opening 6 of frame body 7 on which transmissive component 5 is superposed, with an adhesive for example. Further, it is preferable that a reflector that does not compose a positioning component is provided separately. This increases the light-collection efficiency.

In the above-described embodiment, the description is made of the example where positioning component 11 is provided with linear slope 14, but not limited to the case. For example, the slope may be composed of a curve shape. This further increases the directivity of radiated light.

In the above-described embodiment, the description is made of the example where the circuit of substrate 2 is connected with the circuit part of interposer 3 through wire 10, but not limited to the case. For example, a configuration may be made in which a through hole is formed in the interposer and connection is made through the through hole. This eliminates the need for recess 11d formed, which simplifies the shape of positioning component 11. Further, this increases the workability and reliability in connection.

In the above-described embodiment, it is preferable to make transmissive component 5, frame body 7, and positioning component 11 connect one another in a tight contact manner using sealant 9 such as an adhesive, which is not especially described. This prevents water ingress into substrate 2 more reliably.

As described hereinbefore, a light emitting device of the present disclosure includes a substrate with a circuit incorporated in the substrate, an interposer disposed on the circuit side of the substrate and having a circuit part connected to the circuit of the substrate, a light emitting element disposed on the interposer, and a transmissive component disposed in accordance with the light emitting element. The light emitting device further includes a frame body having an opening in which the transmissive component is disposed, a ring-shaped body disposed so as to encompass the frame body on the substrate, and a sealant making the frame body, substrate, and ring-shaped body tightly contact one another. The frame body may be configured to be disposed so as to encompass the light emitting element on the substrate.

Resultingly, the substrate is covered with the ring-shaped body, sealant, and interposer in an airtight state. This prevents water entering from the outside from adhering onto the circuit of the substrate.

The light emitting device of the present disclosure may further include a positioning component that is in contact with the interposer and determines the position of the transmissive component with respect to the light emitting element.

This allows the position of the transmissive component to be easily determined with respect to the light emitting element.

In the light emitting device of the present disclosure, the positioning component may be composed of a reflector that encompasses the light emitting element inside the frame body.

This allows light emitted from the light emitting element to be efficiently pointed toward the transmissive component.

In a light emitting device of the present disclosure, the sealant may be an adhesive.

This allows the frame body, ring-shaped body, and substrate to be easily and reliably bonded and fastened to one another.

The light emitting device of the present disclosure includes the above-described light emitting device, a case disposed on the substrate and having a ring-shaped part disposed so as to encompass the frame body and the ring-shaped body, and sealing material disposed between the ring-shaped part and the ring-shaped body.

This prevents water entering from the outside from adhering onto the circuit of the substrate, providing a lighting device with high reliability.

INDUSTRIAL APPLICABILITY

The present disclosure is useful for a light emitting device with high waterproof function demanded and for a lighting device for example provided with the light emitting device.

REFERENCE MARKS IN THE DRAWINGS 1 light emitting device
2 substrate
2a surface
3 interposer
4 light emitting element
5 transmissive component
6 opening
7 frame body
7a first end
7b second end
7c inner circumferential surface
7d outer circumferential surface
8 ring-shaped body
8a bottom surface
8b inner circumference
9 sealant
10 wire
11 positioning component
11a outer circumferential surface
11c end face
11d, 13 recess
12 horizontal plane
14 slope
14a, 14b, 17a opening
14c inner circumferential wall
15 projection
16 lighting device
17 ring-shaped part
18 case
19 sealing material
20 gap

The invention claimed is:

1. A light emitting device comprising:
a substrate with a circuit incorporated in the substrate;
an interposer disposed on the substrate and having a circuit part connected to the circuit of the substrate;
a light emitting element disposed on the interposer;
a transmissive component disposed in accordance with the light emitting element;
a frame body having an opening in which the transmissive component is disposed;
a ring-shaped body disposed so as to encompass the frame body on the substrate; and
a sealant making the frame body, the substrate, and the ring-shaped body tightly contact one another,
wherein the frame body is disposed so as to encompass the light emitting element on the substrate, and
wherein the light emitting device further comprises a positioning component that is in contact with the interposer and determines a position of the transmissive component with respect to the light emitting element.

2. The light emitting device of claim 1, wherein the positioning component is composed of a reflector encompassing the light emitting element inside the frame body.

3. The light emitting device of claim 1, wherein the sealant is an adhesive.

4. A lighting device comprising:
the light emitting device of claim 1;
a case disposed on the substrate and having a ring-shaped part disposed so as to encompass the frame body and the ring-shaped body; and
a sealing material disposed between the ring-shaped part and the ring-shaped body.

* * * * *